United States Patent [19]

Van Der Ploeg et al.

[11] Patent Number: 5,550,049
[45] Date of Patent: Aug. 27, 1996

[54] PROCESS FOR IDENTIFYING PARA CATION CHANNEL MODULATORS

[75] Inventors: Leonardus H. T. Van Der Ploeg; Jeffrey W. Warmke, both of Scotch Plains, N.J.

[73] Assignee: Merck & Co., Inc, Rahway, N.J.

[21] Appl. No.: 338,702

[22] Filed: Nov. 10, 1994

[51] Int. Cl.$^6$ .............................. C12N 1/21; C12N 1/15; C12N 5/10; C12N 15/12; C12N 15/63
[52] U.S. Cl. .................................. 435/240.1; 435/254.11; 435/252.3; 435/320.1; 536/23.5
[58] Field of Search ........................ 536/23.5; 435/240.1, 435/252.3, 254.11

[56] References Cited

PUBLICATIONS

Hall and Kasbekar, Drosophila Sodium Channel Mutations Affect Pyrethroid Sensitivity, in Insectide Action, (eds. Narahashi et al.) New York: Plenum Press pp. 99–114. 1981.
Noda, Masaharu et al., Existence of distinct sodium channel messenger RNAs in rat brain, Nature, vol. 320, pp. 188–192 (1986).
Liman, E., et al., Subunit Stoichiometry of a Mammalian K+ Channel Determined by Construction of Multimeric cDNAs, Neuron, vol. 9, pp. 861–871 (1992).
Jackson, F., et al., The tip–E Mutation of Drosophila Decreases Saxitoxin Binding and Interacts with Other Mutations Affecting Nerve Membrane Excitability, Journ. of Neurogenetics, 3, pp. 1–17 (1986).
Taylor, Martin F. J. et al., Linkage of Pyrethroid Insecticide Resistance to a Sodium Channel Locus in the Tobacco Budworm, Insect Biochem. Molec. Biol., vol. 23, No. 7, pp. 763–775, (1993).
Knipple, D. C., et al., Tight genetic linkage between the kdr insecticide resistance trait and a voltage–sensitive sodium channel gene in the house fly, Proc. Natl. Acad. Sci., vol. 91, pp. 2483–2487 (1994).
Williamson, M., et al., Knockdown resistance (kdr) to DDT and pyrethroid insecticides maps to a sodium channel gene locus in the housefly (Musca domestica), Mol. Gen. Genet. 240: pp. 17–22 (1993).
Hall, L. M. et al., Molecular and genetic analysis of tip–E: a mutation affecting sodium channels in Drosophila, 35th Annual Drosophila Res. Conf., Program & Absts. p. 77. (1994).
Hall & Feng, Abstracts of papers presented at the 48th Annual mtg of the society of general physiologists, Marine Biological Lab, The tip–E Locus Defines a Novel Membrane Protein Required During Development to Rescue Adult Paralysis, p. 11a, (1994).

O'Dowd and Aldrich, Voltage–Clamp Analysis of Sodium Channels in Wild–type and Mutant Drosophila Neurons, The Journal of Neuroscience, 8 (10), p. 3633–3643 (1988).
Barry Ganetyzky, Neurogenetic Analysis of Drosophila Mutations Affecting Sodium Channels: Synergistic Effects on Viability and Nerve Conduction in Double Mutants Involving tip–E, Journal of Neurogenetics, 3, pp. 19–31 (1986).
Thackeray and Ganetzky, Developmentally Regulated Alternative Splicing Generates a Complex Array of Drosophila para Sodium Channel Isoforms, The Journal of Neuroscience, 14 (5), pp. 2569–2578 (1994).
Loughney, K., et al., Molecular Analysis of the para Locus, a Sodium Channel Gene in Drosophila, Cell, vol. 58, pp. 1143–1154 (1989).
Ramaswami and Tanouye, Two sodium–channel genes in Drosophila: Implications for channel diversity, Proc. Natl. Acad. Sci., vol. 86, pp. 2079–2082 (1989).
Salkoff, L., et al., Genomic Organization and Deduced Amino Acid Sequence of a Putative Sodium Channel Gene in Drosophila, Science, vol. 237 pp. 744–749 (1987).
Gordon, D., et al., Biochemical Characterization of Insect Neuronal Sodium Channels, Archives of Insect Biochemistry and Physiology 22: pp. 41–53 (1993).
William A. Catterall, Cellular and Molecular Biology of Voltage–Gated Sodium Channels, Physiological Reviews, vol. 72, No. 4 (Suppl.) pp. S15–S48 (1992).
Thummel, C. et al., Vectors for Drosophila P–element–mediated transformation and tissue culture transfection, Gene, 74, pp. 445–456 (1988).
Bunch, T., et al., Characterization and use of the Drosophila metallothionein promoter in cultured Drosophila melanogaster cells, Nucleic Acids Research, vol. 16, No. 3, pp. 1043–1059 (1988).
Noda, M., et al., Primary Structure of Electrophorus Electricus Sodium Channel Deduced from cDNA Sequence, Nature, vol., 312, 8, pp. 121–127 (1984).
Stevens, Charles, And now the sodium channel, Nature, vol. 312, pp. 98–99 (1984).

*Primary Examiner*—Robert A. Wax
*Assistant Examiner*—Gabriele E. Bugalsky
*Attorney, Agent, or Firm*—Jack L. Tribble

[57] ABSTRACT

DNAs encoding voltage-activated cation channels have been cloned and characterized. The cDNA's have been expressed in recombinant host cells which produce active recombinant protein. The recombinant protein is also purified from the recombinant host cells. In addition, the recombinant host cells are utilized to establish a method for identifying modulators of the channel activity, and channel modulators are identified. Channel modulators are useful as insecticides and arachnicidic agents.

3 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GACTCTAGAC GTTGGCCGCA TAGACAATGA CAG       33

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AAGAGCTCGA CGAAGGGATC G                                                                                        2 1

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCTTCGATCC CTTCGTCGAG CTCT                                                                                     2 4

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AAAGGATCCA AATATGATGA A                                                                                        2 1

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TTTGGATCCT TTTTCACACT CAATC                                                                                    2 5

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GACTCTAGAG CTAATACTCG CGTGCATCTT GG                                                                            3 2

( 2 ) INFORMATION FOR SEQ ID NO:7:

( i ) SEQUENCE CHARACTERISTICS:
        ( A ) LENGTH: 6513 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCTAGACGTT GGCCGCATAG ACAATGACAG AAGATTCCGA CTCGATATCT GAGGAAGAAC                                              6 0

GCAGTTTGTT CCGTCCCTTT ACCCGCGAAT CATTGGTGCA AATCGAACAA CGCATTGCCG                                              1 2 0

| | | | | | |
|---|---|---|---|---|---|
| CTGAACATGA | AAAGCAGAAG | GAGCTGGAAA | GAAAGAGAGC | CGAGGGAGAG | GTGCCGCGAT | 180 |
| ATGGTCGCAA | GAAAAAACAA | AAAGAAATCC | GATATGATGA | CGAGGACGAG | GATGAAGGTC | 240 |
| CACAACCGGA | TCCTACACTT | GAACAGGGTG | TGCCAATACC | TGTTCGATTG | CAGGGCAGCT | 300 |
| TCCCGCCGGA | ATTGGCCTCC | ACTCCTCTCG | AGGATATCGA | TCCCTACTAC | AGCAATGTAC | 360 |
| TGACATTCGT | AGTTGTAAGC | AAAGGAAAAG | ATATTTTTCG | CTTTTCTGCA | TCAAAAGCAA | 420 |
| TGTGGATGCT | CGATCCATTC | AATCCGATAC | GTCGTGTGGC | CATTTACATT | CTAGTGCATC | 480 |
| CATTATTTTC | CCTATTCATC | ATCACCACAA | TTCTCGTCAA | CTGCATCCTG | ATGATAATGC | 540 |
| CGACAACGCC | CACGGTTGAG | TCCACTGAGG | TGATATTCAC | CGGAATCTAC | ACATTTGAAT | 600 |
| CAGCTGTTAA | AGTGATGGCA | CGAGGTTTCA | TTTTATGCCC | GTTTACGTAT | CTTAGAGATG | 660 |
| CATGGAATTG | GCTGGACTTC | GTAGTAATAG | CTTTAGCTTA | TGTGACCATG | GGTATAGATT | 720 |
| TAGGTAATCT | AGCAGCCCTG | CGAACGTTTA | GGGTGCTGCG | AGCGCTTAAA | ACCGTAGCCA | 780 |
| TTGTGCCAGG | CTTGAAGACC | ATCGTCGGCG | CCGTCATCGA | ATCGGTGAAG | AATCTGCGCG | 840 |
| ATGTGATTAT | CCTGACCATG | TTCTCCCTGT | CGGTGTTCGC | GTTGATGGGC | CTACAGATCT | 900 |
| ATATGGGCGT | GCTCACCGAG | AAGTGCATCA | AGAAGTTCCC | GCTGGACGGT | TCCTGGGGCA | 960 |
| ATCTGACCGA | CGAGAACTGG | GACTATCACA | ATCGCAATAG | CTCCAATTGG | TATTCCGAGG | 1020 |
| ACGAGGGCAT | CTCATTTCCG | TTATGCGGCA | ATATATCCGG | TGCGGGGCAA | TGCGACGACG | 1080 |
| ATTACGTGTG | CCTGCAGGGG | TTTGGTCCGA | ATCCGAATTA | TGGCTACACC | AGCTTCGATT | 1140 |
| CGTTCGGATG | GGCTTTCCTG | TCCGCCTTCC | GGCTGATGAC | ACAGGACTTC | TGGGAGGATC | 1200 |
| TGTACCAGCT | GGTGTTGCGC | GCCGCCGGAC | CATGGCACAT | GCTGTTCTTT | ATAGTCATCA | 1260 |
| TCTTCCTAGG | TTCATTCTAT | CTTGTGAATT | TGATTTGGC | CATTGTTGCC | ATGTCGTATG | 1320 |
| ACGAATTGCA | AAGGAAGGCC | GAAGAAGAAG | AGGCTGCCGA | AGAGGAGGCG | ATACGTGAAG | 1380 |
| CGGAAGAAGC | TGCCGCCGCC | AAAGCGGCCA | AGCTGGAGGA | GCGGGCCAAT | GCGCAGGCTC | 1440 |
| AGGCAGCAGC | GGATGCGGCT | GCCGCCGAAG | AGGCTGCACT | GCATCCGGAA | ATGGCCAAGA | 1500 |
| GTCCGACGTA | TTCTTGCATC | AGCTATGAGC | TATTTGTTGG | CGGCGAGAAG | GGCAACGATG | 1560 |
| ACAACAACAA | AGAGAAGATG | TCCATTCGGA | GCGTCGAGGT | GGAGTCGGAG | TCGGTGAGCG | 1620 |
| TTATACAAAG | ACAACCAGCA | CCTACCACAG | CACACCAAGC | TACCAAAGTT | CGTAAAGTGA | 1680 |
| GCACGACATC | CTTATCCTTA | CCTGGTTCAC | CGTTTAACAT | ACGCAGGGGA | TCACGTAGTT | 1740 |
| CTCACAAGTA | CACGATACGG | AACGGACGTG | GCCGCTTTGG | TATACCCGGT | AGCGATCGTA | 1800 |
| AGCCATTGGT | ATTGTCAACA | TATCAGGATG | CCCAGCAGCA | CTTGCCCTAT | GCCGACGACT | 1860 |
| CGAATGCCGT | CACCCCGATG | TCCGAAGAGA | ATGGGGCCAT | CATAGTGCCC | GTGTACTATG | 1920 |
| GCAATCTAGG | CTCCCGACAC | TCATCGTATA | CCTCGCATCA | GTCCCGAATA | TCGTATACCT | 1980 |
| CACATGGCGA | TCTACTCGGC | GGCATGGCCG | TCATGGGCGT | CAGCACAATG | ACCAAGGAGA | 2040 |
| GCAAATTGCG | CAACCGCAAC | ACACGCAATC | AATCAGTGGG | CGCCACCAAT | GGCGGCACCA | 2100 |
| CCTGTCTGGA | CACCAATCAC | AAGCTCGATC | ATCGCGACTA | CGAAATTGGC | CTGGAGTGCA | 2160 |
| CGGACGAAGC | TGGCAAGATT | AAACATCATG | ACAATCCTTT | TATCGAGCCC | GTCCAGACAC | 2220 |
| AAACGGTGGT | TGATATGAAA | GATGTGATGG | TCCTGAATGA | CATCATCGAA | CAGGCCGCTG | 2280 |
| GTCGGCACAG | TCGGGCAAGC | GATCGCGGTG | TCTCCGTTTA | CTATTTCCCA | ACAGAGGACG | 2340 |
| ATGACGAGGA | TGGGCCGACG | TTCAAAGACA | AGGCACTCGA | AGTGATCCTC | AAAGGCATCG | 2400 |
| ATGTGTTTTG | TGTGTGGGAC | TGTTGCTGGG | TTTGGTTGAA | ATTTCAGGAG | TGGGTATCGC | 2460 |
| TCATCGTCTT | CGATCCCTTC | GTCGAGCTCT | TCATCACGCT | GTGCATTGTG | GTCAACACGA | 2520 |

| | | | | | |
|---|---|---|---|---|---|
| TGTTCATGGC | AATGGATCAC | CACGATATGA | ACAAGGAGAT | GGAACGCGTG | CTCAAGAGTG | 2580
| GCAACTATTT | CTTCACCGCC | ACCTTTGCCA | TCGAGGCCAC | CATGAAGCTA | ATGGCCATGA | 2640
| GCCCCAAGTA | CTATTTCCAG | GAGGGCTGGA | ACATCTTCGA | CTTCATTATC | GTGGCCCTAT | 2700
| CGCTATTGGA | ACTGGGACTC | GAGGGTGTCC | AGGGTCTGTC | CGTATTGCGT | TCCTTTCGAT | 2760
| TGCTGCGTGT | ATTCAAACTG | GCCAAGTCTT | GGCCCACACT | TAATTTACTC | ATTTCGATTA | 2820
| TGGGACGCAC | CATGGGCGCT | TTGGGTAATC | TGACATTTGT | ACTTTGCATT | ATCATCTTCA | 2880
| TCTTTGCGGT | GATGGGAATG | CAACTGTTCG | GAAAGAATTA | TCATGATCAC | AAGGACCGCT | 2940
| TTCCGGATGG | CGACCTGCCG | CGCTGGAACT | TCACCGACTT | TATGCACAGC | TTCATGATCG | 3000
| TGTTCCGGGT | GCTCTGCGGA | GAATGGATCG | AGTCCATGTG | GGACTGCATG | TACGTGGGCG | 3060
| ATGTCTCGTG | CATTCCCTTC | TTCTTGGCCA | CCGTTGTCAT | CGGCAATCTT | GTGGTACTTA | 3120
| ACCTTTTCTT | AGCCTTGCTT | TTGTCCAATT | TTGGCTCATC | TAGCTTATCA | GCGCCGACTG | 3180
| CCGATAACGA | TACGAATAAA | ATAGCCGAGG | CCTTCAATCG | AATTGGCCGA | TTTAAAAGTT | 3240
| GGGTTAAGCG | TAATATTGCT | GATTGTTTCA | AGTTAATACG | TAACAAATTG | ACAAATCAAA | 3300
| TAAGTGATCA | ACCATCAGGT | GAGAGGACCA | ACCAGATCAG | TTGGATTTGG | AGCGAAGAGC | 3360
| ATGGTGACAA | CGAACTGGAG | CTGGGCCACG | ACGAGATCCT | CGCCGACGGC | CTCATCAAGA | 3420
| AGGGGATCAA | GGAGCAGACG | CAACTGGAGG | TGGCCATCGG | GGATCGGATG | GAATTCACGA | 3480
| TACACGGCGA | CATGAAGAAC | AACAAGCCGA | AGAAATCCAA | ATATCTAAAT | AACGCAACGA | 3540
| TGATTGGCAA | CTCAATTAAC | CACCAAGACA | ATAGACTGGA | ACACGAGCTA | AACCATAGAG | 3600
| GTTTGTCCTT | ACAGGACGAC | GACACTGCCA | GCATTAACTC | ATATGGTAGC | CATAAGAATC | 3660
| GACCATTCAA | GGACGAGAGC | CACAAGGGCA | GCGCCGAGAC | GATGGAGGGC | GAGGAGAAGC | 3720
| GCGACGCCAG | CAAGGAGGAT | TTAGGTCTCG | ACGAGGAACT | GGACGAGGAG | GGCGAATGCG | 3780
| AGGAGGGCCC | GCTCGACGGT | GATATCATTA | TTCATGCACA | CGACGAGGAT | ATACTCGATG | 3840
| AATATCCAGC | TGATTGCTGC | CCCGATTCGT | ACTATAAGAA | ATTTCCGATC | TTAGCCGGTG | 3900
| ACGATGACTC | GCCGTTCTGG | CAAGGATGGG | GCAATTTACG | ACTGAAAACT | TTTCAATTAA | 3960
| TTGAAAATAA | ATATTTTGAA | ACAGCTGTTA | TCACTATGAT | TTTAATGAGT | AGCTTAGCTT | 4020
| TGGCATTAGA | AGATGTACAT | CTGCCACAAA | GACCCATACT | GCAGGATATT | TTATACTATA | 4080
| TGGACAGAAT | ATTTACGGTT | ATATTCTTCT | GGAAATGTT | AATCAAGTGG | TTGGCGCTCG | 4140
| GCTTCAAAGT | GTACTTCACC | AACGCGTGGT | GTTGGCTCGA | TTTCGTGATT | GTCATGGTAT | 4200
| CGCTTATCAA | CTTCGTTGCT | TCACTTGTTG | GAGCTGGTGG | TATTCAAGCC | TTCAAGACTA | 4260
| TGCGAACGTT | AAGAGCACTG | AGACCACTAC | GTGCCATGTC | CCGTATGCAG | GGCATGAGGG | 4320
| TCGTCGTTAA | TGCGCTGGTA | CAAGCTATAC | CGTCCATCTT | CAATGTGCTA | TTGGTGTGTC | 4380
| TAATATTTTG | GCTAATTTTT | GCCATAATGG | GTGTACAGCT | TTTTGCTGGA | AAATATTTTA | 4440
| AGTGCGAGGA | CATGAATGGC | ACGAAGCTCA | GCCACGAGAT | CATACCAAAT | CGCAATGCCT | 4500
| GCGAGAGCGA | GAACTACACG | TGGGTGAATT | CAGCAATGAA | TTTCGATCAT | GTAGGTAACG | 4560
| CGTATCTGTG | CCTTTTCCAA | GTGGCCACCT | TCAAAGGCTG | GATACAAATC | ATGAACGATG | 4620
| CTATCGATTC | ACGAGAGGTG | GACAAGCAAC | CAATTCGTGA | AACGAACATC | TACATGTATT | 4680
| TATATTTCGT | ATTCTTCATC | ATATTTGGAT | CCTTTTTCAC | ACTCAATCTG | TTCATTGGTG | 4740
| TTATCATTGA | TAATTTTAAT | GAGCAAAAGA | AAAAGCAGG | TGGATCATTA | GAAATGTTCA | 4800
| TGACAGAAGA | TCAGAAAAAG | TACTATAATG | CTATGAAAAA | GATGGGCTCT | AAAAAACCAT | 4860
| TAAAAGCCAT | TCCAAGACCA | AGGTGGCGAC | CACAAGCAAT | AGTCTTTGAA | ATAGTAACCG | 4920

```
ATAAGAAATT  CGATATAATC  ATTATGTTAT  TCATTGGTCT  GAACATGTTC  ACCATGACCC   4980
TCGATCGTTA  CGATGCGTCG  GACACGTATA  ACGCGGTCCT  AGACTATCTC  AATGCGATAT   5040
TCGTAGTTAT  TTTCAGTTCC  GAATGTCTAT  TAAAAATATT  CGCTTTACGA  TATCACTATT   5100
TTATTGAGCC  ATGGAATTTA  TTTGATGTAG  TAGTTGTCAT  TTTATCCATC  TTAGGTCTTG   5160
TACTTAGCGA  TATTATCGAG  AAGTACTTCG  TGTCGCCGAC  CCTGCTCCGA  GTGGTGCGTG   5220
TGGCGAAAGT  GGGCCGTGTC  CTTCGACTGG  TGAAGGGAGC  CAAGGGCATT  CGGACACTGC   5280
TCTTCGCGTT  GGCCATGTCG  CTGCCGGCCC  TGTTCAACAT  CTGCCTGCTG  CTGTTCCTGG   5340
TCATGTTCAT  CTTTGCCATT  TTCGGCATGT  CGTTCTTCAT  GCACGTGAAG  GAGAAGAGCG   5400
GCATTAACGA  CGTCTACAAC  TTCAAGACCT  TGGCCAGAG   CATGATCCTG  CTCTTTCAGA   5460
TGTCGACGTC  AGCCGGTTGG  GATGGTGTAC  TGGACGCCAT  TATCAATGAG  GAAGCATGCG   5520
ATCCACCCGA  CAGCGACAAA  GGCTATCCGG  GCAATTGTGG  TTCAGCGACC  GTTGGAATAA   5580
CGTTTCTCCT  CTCATACCTA  GTTATAAGCT  TTTTGATAGT  TATTAATATG  TACATTGCTG   5640
TCATTCTCGA  GAACTATAGT  CAGGCCACCG  AGGACGTGCA  AGAGGGTCTA  ACCGACGACG   5700
ACTACGACAT  GTACTATGAG  ATCTGGCAGC  AATTCGATCC  GGAGGGCACC  CAGTACATAC   5760
GCTATGATCA  GCTGTCCGAA  TTCCTGGACG  TACTGGAGCC  CCCGCTGCAG  ATCCACAAAC   5820
CGAACAAGTA  CAAGATCATA  TCGATGGACA  TACCCATCTG  TCGCGGTGAC  CTCATGTACT   5880
GCGTCGACAT  CCTCGACGCC  CTTACGAAAG  ACTTCTTTGC  GCGGAAGGGC  AATCCGATAG   5940
AGGAGACGGG  TGAGATTGGT  GAGATAGCGG  CCCGCCCGGA  TACGGAGGGC  TACGAGCCCG   6000
TCTCATCAAC  GCTGTGGCGT  CAGCGTGAGG  AGTACTGCGC  CCGGCTAATC  CAGCACGCCT   6060
GGCGAAAGCA  CAAGGCGCGC  GGCGAGGGAG  GTGGGTCCTT  TGAGCCGGAT  ACGGATCATG   6120
GCGATGGCGG  TGATCCGGAT  GCCGGGGACC  CGGCGCCCGA  TGAAGCAACG  GACGGCGATG   6180
CGCCGCTGG   TGGAGATGGT  AGTGTTAACG  GTACTGCAGA  AGGAGCTGCC  GATGCCGATG   6240
AGAGTAATGT  AAATAGTCCG  GGTGAGGATG  CAGCGGCGGC  GGCAGCAGCA  GCAGCAGCAG   6300
CGGCGGCGGC  GGGCACGACG  ACGGCGGGAA  GTCCGGAGC   GGGTAGCGCC  GGGCGACAGA   6360
CCGCCGTTCT  CGTGGAGAGC  GACGGGTTCG  TGACGAAGAA  CGGCCACAAG  GTGGTCATCC   6420
ACTCGCGATC  GCCGAGCATC  ACGTCGCGCA  CGGCGGATGT  CTGAGCCAGG  CCTCGCCCCC   6480
CCCTCCAAGA  TGCACGCGAG  TATTAGCTCT  AGA                                  6513
```

PROCESS FOR IDENTIFYING PARA CATION CHANNEL MODULATORS

BACKGROUND OF THE INVENTION

Voltage-activated sodium channels are responsible for the fast depolarizing phase of the action potential that underlies electrical signaling in neurons, muscles and other electrically excitable cells (reviewed by Hille, 1992 Ionic Channels of Excitable Membranes (Sinauer, Sunderland, Mass.)). Biochemical characterization of voltage-activated sodium channels from a variety of tissues indicate that they all contain a single alpha subunit of molecular weight ranging from 230,000 to 300,000 (reviewed by Catterall, 1992 Cellular and Molecular Biology of Voltage-gated Sodium Channels. Physiological Reviews, 72:S15-S48). The alpha subunit of the Electrophorus electricus voltage-activated sodium channel was cloned using biochemical and molecular genetic techniques (Noda, et al., 1984 Primary structure of Electrophorus electricus sodium channel deduced from cDNA sequence. Nature, 312:121–127.). The purified Electrophorus electricus sodium channel alpha subunit forms a functional voltage-activated sodium channel as a single alpha subunit (Rosenberg, R. L., et al., 1984, Proc. Natn. Acad. Sci. U.S.A. 1:1239-1243). The cDNA encoding the Electrophorus electricus voltage-activated sodium channel was used to isolate cDNAs encoding three distinct, but highly homologous rat brain voltage-activated sodium channel genes (Kayano et al., 1988, Primary structure of rat brain sodium channel III deduced from the cDNA sequence, FEBS Lett. 228:187–194; Noda et al. 1986, Nature .320;188–192). Biochemical analysis of voltage-activated sodium channels from rat brain indicate that the alpha subunits am associated noncovalently with a beta1 subunit (36,000 kDa) and are disulfide linked to a beta2 subunit (33,000 kDa) which is not required for channel activity (Hartshorne and Catterall, 1981, Purification of the saxitoxin receptor of the sodium channel from rat brain. Proc. Natl. Acad. Sci. U.S.A. 78:4620–4624; Hartshorne and Catterall 1984, The sodium channel from rat brain. Purification and subunit composition. J. Biol. Chem. 259:1667–1675; Hartshorne, et al., 1982, The saxitoxin receptor of the sodium channel from rat brain. Evidence for two nonidentical beta subunits. J. Biol. Chem. 257:13888–13891; Messsner and Catterall, 1985, The sodium channel from rat brain. Separation and characterization of subunits. J. Biol. Chem. 260:10597–10604). RNAs transcribed from cDNAs encoding alpha subunits of mammaliam voltage-activated sodium channels are sufficient to direct the synthesis of functional sodium channels when injected into Xenopus oocytes (Auld et al. 1988, A rat brain Na+channel alpha subunit with novel gating properties. Neuron 1:448–461; Moorman et al. 1990, Changes in sodium channel gating produced by point mutations in a cytoplasmic linker. Science 250:688–691; Noda et al. 1986, Expression of functional sodium channels from cloned cDNA. Nature 322:826–828; Suzuki et al. 1988, Functional expression of cloned cDNA encoding sodium channel III. FEBS Lett. 228:195–200). Although alpha subunits of mammalian voltage-activated sodium channels are sufficient to encode functional sodium channels in Xenopus oocytes, their biophysical properties are not identical to those observed in intact cells. Co-expression of the rat brain voltage-activated sodium channel beta1 subunit with the rat brain type IIa alpha subunit in Xenopus oocytes restores the normal biophysical properties observed in intact cells (Isom et al. 1992, Primary structure and functional expression of the B 1 subunit of the rat brain sodium channel. Science 256: 839–842).

Biochemical characterization of insect neuronal sodium channels has revealed that they contain an alpha subunit of molecular weight ranging from 240,000 to 280,000, but they lack any covalently linked beta subunits (Gordon et al 1993, Biochemical Characterization of Insect Neuronal Sodium Channels. Archives of Insect Biochemistry and Physiology 22:41–53). Partial DNA sequences from the fruit fly *Drosophila melanogaster* presumed to encode voltage-activated sodium channels were initially identified on the basis of homology to vertebrate voltage-activated sodium channel alpha subunits (Salkoff et al. 1987, Genomic organization and deduced amino acid sequence of a putative sodium channel genes in Drosophila. Science 237:744–749; Okamoto et al. 1987, Isolation of Drosophila genomic clones homologous to the eel sodium channel gene. Proc. Jpn. Acad. 63(B):284–288; Ramaswami and Tanouye, 1989, Two sodium-channel gene in Drosophila: Implications for channel diversity. Proc. Natn. Acad. Sci. U.S.A. 86:2079–2082). Using a molecular genetic approach it was determined that the paralytic (para) locus in Drosophila encodes a voltage-activated sodium channel alpha subunit and the entire para cDNA sequence was determined (Loughney et al. 1989, Molecular analysis of the para locus, a sodium channel gene in Drosophila. Cell 58:1143–1154; Thackeray and Ganetzky 1994, Developmentally regulated alternative splicing generates a complex array of Drosophila para sodium channel isoforms. J. Neuroscience 14:2569–2578).

It has been proposed that the Drosophila ripe locus encodes a regulatory or structural component of voltage-activated sodium channels for the following reasons: (1) [3H] saxitoxin binding to voltage-activated sodium channels is reduce 30–40% in tipE mutants (Jackson et al. 1986, The tipE mutation of Drosophila decreases saxitoxin binding and interacts with other mutations affecting nerve membrane excitability. J. of Neurogenetics, 3:1–17), (2) sodium current density is reduced 40–50% in cultured embryonic neurons from tipE mutants (O'Dowd and Aldrich, 1988, Voltage-Clamp Analysis of Sodium Channels in wild-type and Mutant Drosophila Neurons. J. of Neuroscience, 8:3633–3643), (3) para;tipE mutants exhibit unconditional lethality in an allele specific manner (Ganetzky 1986, Neurogenetic analysis of Drosophila Mutations affecting Sodium Channels: Synergistic Effects on Viability and Nerve Conduction in Double Mutants involving tipE. J. of Neurogenetics, 3:19–31. Jackson et al. 1986, The tipE mutation of Drosophila decreases saxitoxin binding and interacts with other mutations affecting nerve membrane excitability. J. of Neurogenetics, 3:1–17), (4) para and tipE RNA are expressed in the embryonic CNS and PNS (Hall et al. 1994, Molecular and genetic analysis of tipE: a mutation affecting sodium channels in Drosophila. Presented at the 351h Annual Drosophila Research Conference, Apr. 20–24, 1994, Chicago, Ill.; Hong and Ganetzky 1994, Spatial and temporal expression patterns of two sodium channel genes in Drosophila. J. Neuroscience, 14:5160-5169), (5) ripe encodes a 50kDa acidic protein with two putative membrane spanning domains, a membrane topology shared by other ion channel subunits (Hall et al. 1994, Molecular and genetic analysis of tipE: a mutation affecting sodium channels in Drosophila. Presented at the 351h Annual Drosophila Research Conference, Apr. 20–24, 1994, Chicago, Ill.; Hall and Feng 1994, The ripe locus defines a novel membrane protein required during development to rescue adult paralysis. Presented at the 481h annual meeting of the Society of General Physiologists, Sep. 7–11, 1994, Woods Hole Mass.).

The Drosophila ripe locus has been cloned and sequenced but the nucleotide and amino acid sequence of ripe are presently undisclosed (Hall et al. 1994, Molecular and genetic analysis of tipE: a mutation affecting sodium channels in Drosophila. Presented at the 35lh Annual Drosophila Research Conference, Apr. 20–24, 1994, Chicago, Ill.; Hall and Feng 1994, The tipE locus defines a novel membrane protein required during development to rescue adult paralysis (para). Presented at the 481h annual meeting of the Society of General Physiologists, Sep. 7–11, 1994, Woods Hole Mass.).

SUMMARY OF THE INVENTION

Using a recombinant expression system, it has been shown that functional expression of Drosophila para voltage-activated sodium channels requires the co-expression of the para alpha subunit with tipE, a putative Drosophila voltage-activated sodium channel beta subunit. The electrophysiological and pharmachological properties of the Drosophila para voltage-activated sodium channel is disclosed. Recombinant host cells expressing the Drosophila para voltage-activated sodium channel are useful in the identification of modulators of insect voltage-activated sodium channels. Modulators of voltage-activated sodium channels are useful as insecticides and therapeutic agents. Voltage-activated sodium channel para homologs from other arthropod species are likely to also require coexpression with the corresponding tipE homolog for functional expression.

DETAILED DESCRIPTION OF THE INVENTION

Figure 1:
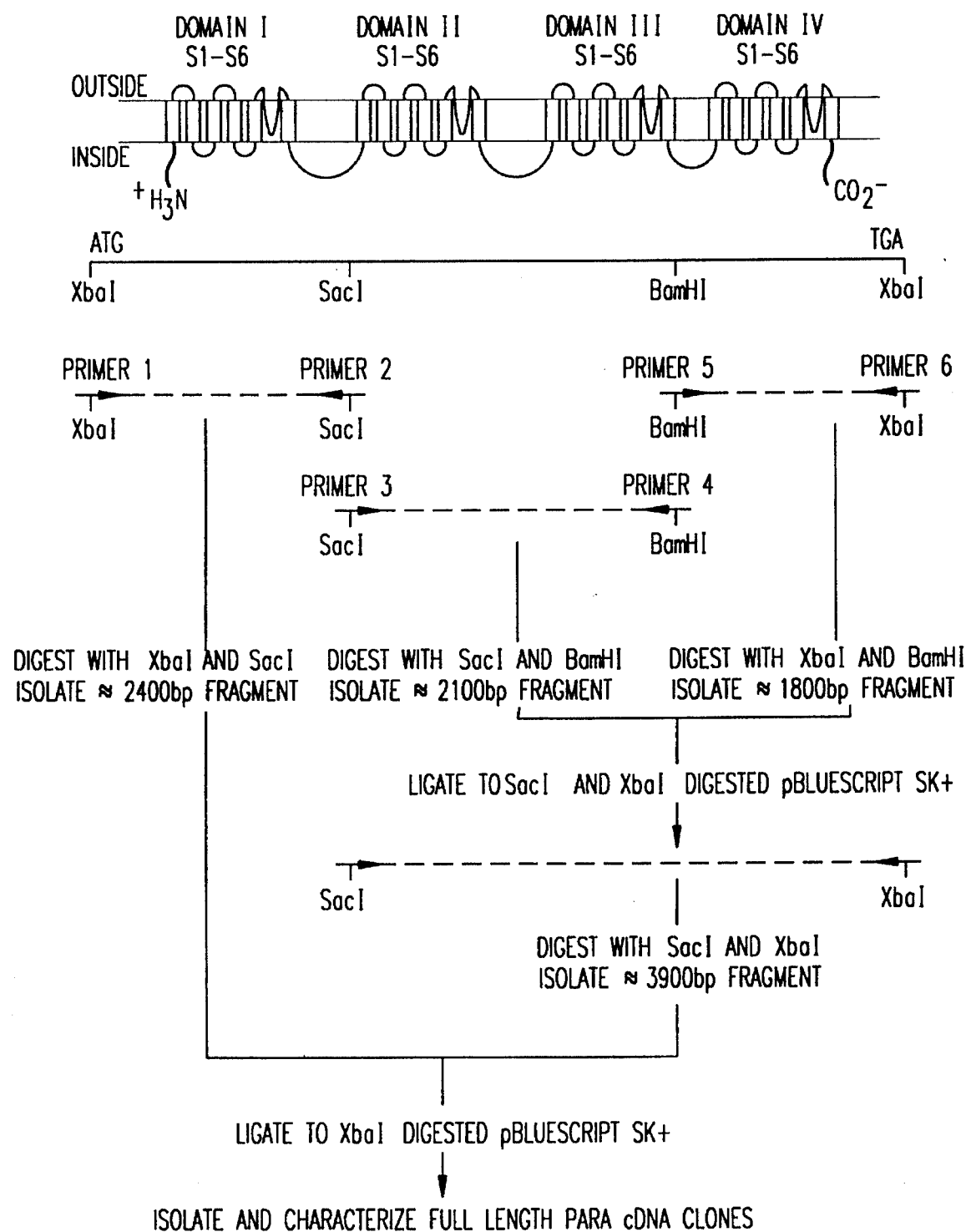
FIG. 1—PCR amplification and assemble of a full length para cDNA is shown.

The present invention relates to coexpression of para and tipE cDNAs encoding a Drosophila voltage-activated sodium channel. The present invention is also related to recombinant host cells which coexpress the cloned para and tipE encoding DNAs contained in recombinant expression plasmids. The present invention is also related to a method for the screening of substances which modulate Drosophila voltage-activated sodium channel activity. The amino acid sequence of para and the DNA encoding para were previously known (Loughney et al. 1989, Molecular analysis of the para locus, a sodium channel gene in Drosophila. Cell 58:1143–1154; Thackeray and Ganetzky 1994, Developmentally Regulated alternative splicing generates a complex array of Drosophila para sodium channel isoforms. J. Neuroscience 14:2569–2578) and PCR generated full length para cDNA clones are described herein (see FIG. 1 )

Partial DNA sequences from the insect, *Drosophila melanogaster* presumed to encode voltage-activated sodium channels were initially identified on the basis of homology to vertebrate voltage-activated sodium channel alpha subunits (Salkoff et al. 1987, Genomic organization and deduced amino acid sequence of a putative sodium channel genes in Drosophila. Science 237:744–749; Okamoto et al. 1987, Isolation of Drosophila genomic Clones homologous to the eel sodium channel gene. Proc. Jpn. Acad. 63(B):284–288; Ramaswami and Tanouye, 1989, Two sodium-channel gene in Drosophila: Implications for channel diversity. Proc. Natn. Acad. Sci. U.S.A. 86:2079–2082). Using a molecular genetic approach it was determined that the para locus in Drosophila encodes a voltage-activated sodium channel alpha subunit and the entire para cDNA sequence was determined from a series of overlapping cDNA clones (Loughney et al. 1989, supra, Thackeray and Ganetzky 1994, supra). It is readily apparent to those skilled in the art that a number of approaches could be used to assemble a full length para cDNA for functional expression studies. These methods include, but are not limited to, assembling the available partial cDNAs into a full length cDNA, using the existing cDNA clones to screen a Drosophila cDNA library to isolate a full length cDNA, PCR amplification of a full length cDNA using primers based on the published sequence. The actual method employed for the invention described herein is summarized in FIG. 1 and FIG. 2.

It is readily apparent to those skilled in the art that suitable cDNA libraries may be prepared from tissue derived from any developmental stage of Drosophila which have voltage-activated sodium channel activity or any Drosophila cell line exhibiting voltage-activated sodium channel activity. The selection of tissues or cell lines for use in preparing a cDNA library to isolate para cDNA may be done by first measuring para expression using the known para DNA sequence or available para cDNAs to generate a probe.

Preparation of cDNA libraries and analysis of para expression can be performed by standard techniques well known in the art. Well known cDNA library construction techniques and RNA analysis techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982). Well know techniques for PCR amplification of DNA and RNA can be found for example, in Innis, M. A., Gelfand, D. H., Sninsky, J. J., White, T. J., PCR Protocols: A Guide to Methods and Applications (Academic Press, Inc., San Diego, Calif., 1990).

The nucleotide and deduced amino acid sequence of tipE are presently undisclosed; however, the DNA encoding tipE has been cloned and sequenced (Hall et al. 1994, Molecular and genetic analysis of tipE: a mutation affecting sodium channels in Drosophila. Presented at the 35th Annual Drosophila Research Conference, Apr. 20–24, 1994, Chicago, Ill.; Hall and Feng 1994, The tipE locus defines a novel membrane protein required during development to rescue adult paralysis. Presented at the 48th annual meeting of the Society of General Physiologists, Sep. 7–11, 1994, Woods Hole Mass.) and was used to provide tipE RNA for use herein.

It is readily apparent to those skilled in the art that a number of approaches can be used to clone the Drosophila tipE locus. These methods include, but are not limited to, chromosome walking to identify chromosomal rearrangements associated with a tipE mutation followed by isolating a cDNA corresponding to the transcription unit disrupted by the chromosomal rearrangement (as described by Hall et al. 1994, supra). Another method is to generate tipE mutations with transposable element insertions followed by cloning of the DNA flanking the transposible element insertion and using this DNA to screen a Drosophila head specific cDNA library which is enriched in clones derived from neuronal RNAs.

Cloning of Drosophila genes can be performed by standard techniques well know in the art. Well known Drosophila molecular genetic techniques can be found for example, in Roberts, D. B., Drosophila A Practical Approach (IRL Press, Washington, D.C., 1986). Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N. Y., 1982).

Purified biologically active para voltage-activated sodium channels may have several different physical forms. Para and tipE may exist as a full-length nascent or unprocessed polypeptide, or as partially processed polypeptides or combinations of processed polypeptides. Para and/or tipE may be encoded by differentially spliced RNAs leading to different para and/or tipE protein isoforms with different primary amino acid sequences. The full-length nascent para and/or tipE polypeptide may be postranslationally modified by specific proteolytic cleavage events which result in the formation of fragments of the full length nascent polypeptide. A fragment, or physical association of fragments may have the full biological activity associated with para and tipE (voltage-activated sodium channel) however, the degree of sodium channel activity may vary between individual para and tipE fragments and physically associated para and tipE polypeptide fragments.

Biologically active para voltage-activated cation channels may be encoded by a variety of alternatively spliced mRNA. Expression of the alternatively spliced para mRNA may result in different biologically active isoforms of the para channel (Thackeray and Ganetzky, 1994, supra). These isoforms of para may not require the tipE subunit for biological activity. Various isoforms of para are intended to be encompassed by the present invention provided that the para isoform has the biological activity described herein. In addition, biologically active para voltage-activated sodium channels may have several different physical forms. The active para voltage-activated sodium channel may exist as a complex containing both para and tipE polypeptides, or the active para voltage-activated sodium channel may consist of para alone.

The cloned para and tipE cDNAs obtained through the methods described above may be recombinantly expressed by molecular cloning into an expression vector containing a suitable promoter and other appropriate transcription regulatory elements, and transferred into prokaryotic or eukaryotic host cells to produce recombinant para and tipE. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, fungal cells, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant para and tipE in mammalian cells. Commercially available mammalian expression vectors which may be suitable for recombinant para and tipE expression, include but are not limited to, pMAMneo (Clontech), pMC1neo, pXT1, pSG5 (Stratagene), pcDNAI, pcDNAIamp, pcDNA3 (Invitrogen), EBO-pSV2-neo (ATCC 37593) pBPV-1 (8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565)

A variety of bacterial expression vectors may be used to express recombinant para and tipE in bacterial cells. Commercially available bacterial expression vectors which may be suitable for recombinant expression include, but are not limited to, pET vectors (Novagen) and pQE vectors (Qiagen).

A variety of fungal cell expression vectors may be used to express recombinant para and tipE in fungal cells such as yeast. Commercially available fungal cell expression vectors which may be suitable for recombinant expression include, but are not limited to, pYES2 (Invitrogen) and Pichia expression vector (Invitrogen).

A variety of insect cell expression vectors may be used to express recombinant para and tipE in insect cells. Commercially available insect cell expression vectors which may be suitable for recombinant expression include, but are not limited to, pBlueBacII (Invitrogen).

DNA encoding para and tipE may also be cloned into an expression vector for expression in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila (Schneider-2, Kc, etc.) and silkworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651 ), CHO-K1 (ATCC CCL 61 ), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce para and tipE protein. Identification of para and tipE expressing host cell clones may be done by several means, including but not limited to immunological reactivity with anti-para or anti-tipE antibodies, and the presence of host cell-associated voltages activated sodium channel activity.

Expression of para and tipE DNA may also be performed using in vitro produced synthetic mRNA. Synthetic mRNA or mRNA isolated from para voltage-activated sodium channel producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

While functional expression of the para cation channel in Xenopus oocytes required the coexpression of tipE, other expression systems in other recombinant host cells may not require coexpression with tipE. Such alternate expression systems and host cells include, but are not limited to, mammalian cells, insect cells, fungal cells, and bacterial cells.

To determine the para and tipE DNA sequence(s) that yields optimal levels of voltage-activated sodium channel activity and/or sodium channel protein, para and tipE DNA molecules including, but not limited to, the following can be constructed: the full-length open reading frame of the para and tipE cDNA and various constructs containing portions of the cDNA encoding only specific domains of the ion channel proteins or rearranged domains of the proteins, or alternative splice forms of para or tipE. All constructs can be designed to contain none, all or portions of the 5' and/or 3' untranslated region of the para and/or tipE cDNAs. Voltage-activated sodium channel activity and levels of protein expression can be determined following the introduction, both singly and in combination, of these constructs into appropriate host cells. Following determination of the para and tipE cDNA cassettes yielding optimal expression in transient assays, these para and tipE cDNA constructs are transferred to a variety of expression vectors (including recombinant viruses), including but not limited to those for mammalian cells, plant cells, insect cells, oocytes, baculovirus-infected insect cells, *E. coli*, and the yeast *S. cerevisiae*.

Host cell transfectants and microinjected oocytes may be assayed for both the levels of voltage-activated sodium channel activity and levels of para and tipE protein by the following methods. In the case of recombinant host cells, this involves the co-transfection of one or possibly two or more plasmids, containing the para and tipE DNA. In the case of oocytes, this involves the co-injection of synthetic RNAs for para and tipE. Following an appropriate period of time to allow for expression, cellular protein is metabolically labelled with for example $^{35}$S-methionine for 24 hours, after which cell lysates and cell culture supernatants are harvested and subjected to immunprecipitation with polyclonal antibodies directed against the para and/or tipE proteins.

Other methods for detecting para activity involve the direct measurement of voltage-activated sodium channel activity in whole or fractionated cells transfected with para and tipE cDNA or oocytes injected with para and tipE mRNA. Voltage-activated sodium channel activity is measured by membrane depolarization and electrophysiological characteristics of the host cells expressing para and tipE DNA. In the case of recombinant host cells expressing para and tipE, patch voltage clamp techniques can be used to measure sodium channel activity and quantitate para and tipE protein. In the case of oocytes patch clamp as well as two electrode voltage clamp techniques can be used to measure sodium channel activity and quantitate para and tipE protein.

Levels of para and tipE protein in host cells are quantitated by immunoaffinity and/or ligand affinity techniques. Cells expressing para and tipE can be assayed for the number of para molecules expressed by measuring the amount of radioactive saxitoxin binding to cell membranes. para- or tipE-specific affinity beads or para-or tipE-specific antibodies are used to isolate for example $^{35}$S-methionine labelled or unlabelled sodium channel proteins. Labelled para and tipE proteins are analyzed by SDS-PAGE. Unlabelled para and tipE proteins are detected by Western blotting, ELISA or RIA assays employing para or tipE specific antibodies.

Following expression of para and tipE in a recombinant host cell, para and tipE protein may be recovered to provide para sodium channels in active form. Several para sodium channel purification procedures are available and suitable for use. As described herein for purification of para from natural sources, recombinant para may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant para can be separated from other cellular proteins by use of an immunoaffinity column made with monoclonal or polyclonal antibodies specific for full length nascent para, polypeptide fragments of para or para subunits.

Monospecific antibodies to para or tipE are purified from mammalian antisera containing antibodies reactive against para or tipE or are prepared as monoclonal antibodies reactive with para or tipE using the technique of Kohler and Milstein, Nature 256: 495-497 (1975). Monospecific antibody as used herein is defined as a single antibody species or multiple antibody species with homogenous binding characteristics for para or tipE. Homogenous binding as used herein refers to the ability of the antibody species to bind to a specific antigen or epitope, such as those associated with the para or tipE, as described above. Para or tipE specific antibodies are raised by immunizing animals such as mice, rats, guinea pigs, rabbits, goats, horses and the like, with rabbits being preferred, with an appropriate concentration of para or tipE either with or without an immune adjuvant.

Preimmune serum is collected prior to the first immunization. Each animal receives between about 0.1 mg and about 1000 mg of para or tipE associated with an acceptable immune adjuvant. Such acceptable adjuvants include, but are not limited to, Freund's complete, Freund's incomplete, aim-precipitate, water in oil emulsion containing *Corynebacterium parvum* and tRNA. The initial immunization consists of para or tipE in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with para or tipE are prepared by immunizing inbred mice, preferably Balb/c, with para or tipE. The mice are immunized by the IP or SC route with about 0.1 mg to about 10 mg, preferably about 1 mg, of para or tipE in about 0.5 ml buffer or saline incorporated in an equal volume of an acceptable adjuvant, as discussed above. Freund's complete adjuvant is preferred.

The mice receive an initial immunization on day 0 and are rested for about 3 to about 30 weeks. Immunized mice are given one or more booster immunizations of about 0.1 to about 10 mg of para in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatants fluids are collected from growth positive wells on about days 14, 18, and 21 and are screened for antibody production by an immunoassay such as solid phase immunoradioassay (SPIRA) using para or tipE as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-para or anti-tipE mAb is carried out by growing the hydridoma in DMEM containing about 2% fetal calf serum to obtain sufficient quantifies of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of para or tipE in body fluids or tissue and cell extracts.

It is readily apparent to those skilled in the an that the above described methods for producing monospecific antibodies may be utilized to produce antibodies specific for para or tipE polypeptide fragments, or full-length nascent para or tipE polypeptide, or the individual para or tipE subunits. Specifically, it is readily apparent to those skilled in the art that monospecific antibodies may be generated which are specific for only para or tipE or the fully functional voltage-activated sodium channel.

Para and tipE antibody affinity columns are made by adding the antibodies to Affigel-10 (Biorad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing para and tipE or only one subunit are slowly passed through the column. The column is then washed with phosphate buffered saline until the optical density (A280) falls to background, then the protein is eluted with 0.23M glycine-HCl (pH 2.6). The purified para or tipE protein is then dialyzed against phosphate buffered saline.

When coexpressed in Xenopus oocytes para and tipE encode proteins that produce a voltage-activated sodium channel that is blocked by tetrodotoxin. The novel Drosophila voltage-activated sodium channel of the present invention is suitable for use in an assay procedure for the identification of compounds which modulate sodium channel activity. Modulating sodium channel activity, as described herein includes the inhibition or activation of the channel and also includes directly or indirectly affecting the normal regulation of the sodium channel activity. Compounds which modulate the sodium channel activity include agonists, antagonists and compounds which directly or indirectly affect regulation of the sodium channel activity.

The Drosophila voltage-activated sodium channel of the present invention may be obtained from both native and recombinant sources for use in an assay procedure to identify receptor modulators. In general, an assay procedure to identify insect sodium channel modulators will contain the para voltage-activated sodium channel of the present invention, and a test compound or sample which contains a putative sodium channel modulator. The test compounds or samples may be tested directly on, for example, purified sodium channel protein whether native or recombinant, subcellular fractions of sodium channel-producing cells whether native or recombinant, and/or whole cells expressing the sodium channel whether native or recombinant. The test compound or sample may be added to the sodium channel in the presence or absence of a known labelled or unlabelled sodium channel modulator. The modulating activity of the test compound or sample may be determined by, for example, analyzing the ability of the test compound or sample to bind to the sodium channel, activate the sodium channel, inhibit sodium channel activity, inhibit or enhance the binding of other compounds to the sodium channel, modify sodium channel regulation, modify an intracellular activity, or kill the cell expressing the sodium channel.

It is likely that para and tipE related genes in other arthropods encode subunits of voltage-activated sodium channels and that functional expression of the homologous para sodium channel in these species will also require co-expression with the homologous tipE subunit. Para homologs have been partially cloned and characterized in the house fly, *Musca domestica*, (Williamson et al. 1993, Knockdown resistance (kdr) to DDT and pyrethroid insecticides maps to a sodium channel gene locus in the housefly (*Musca domestica*). Mol Gen Genet 240:17–22; Knipple et al., 1994, Tight genetic linkage between the kdr insecticide resistance trait and a voltage-sensitive sodium channel gene in the house fly. Proc. Natn. Acad. Sci. U.S.A. 91:2483–2487) and in the tobacco budworm, *Heliothis virescens* (Taylor et al. 1993, Linkage of pyrethroid insecticide resistance to a sodium channel locus in the tobacco budworm. Insect Biochem. Molec. Biol. 23:763–775); these para homologs share 92% and 89% identity to the *Drosophila melanogaster* para gene, respectively. The high degree of amino acid identity shared by these para homologs may be indicative of the structural and functional conservation of para sodium channels between insects. Furthermore, resistance to pyrethroid insecticides maps to the para locus in all three species (Hall, L. and Kasbekar, D, 1989, in: Insecticide Action, pp. 99–114, Narahashi and Chambers (eds.), Plenum Press, New York; Williamson et al., supra; Knipple et al., supra; Taylor et al., supra); therefore, it is likely that functional expression of all insect para voltage-activated sodium channels will require co-expression with tipE.

The identification of modulators of para sodium channel activity are useful as insecticides and arachnicides. Selective modulators, antagonists or agonists of the insect sodium channel may be used to combat agricultural pests which attack crops either in the field or in storage, pests that attack forestry stock, insect pest infestations in general, nematodes, or fungi which infect plants and/or animals. The compounds are applied for such uses as sprays, dusts, emulsions and the like either to the growing plants or the harvested crops. The techniques for applying these compounds in this manner are known to those skilled in the agricultural arts. Selective modulators, antagonists or agonists of the insect sodium channel may also be used in the prevention and treatment of parasitic infections in humans and domestic animals by ectoparasites such as ticks, mites, lice, fleas and the like. The techniques for administering these compounds to animals and humans are known to those skilled in the veterinary and human health fields, respectively. Other compounds may be useful for stimulating or inhibiting the activity of the sodium channels. Selective antagonists of human sodium channels may be useful as neuro-protective agents for the treatment of stroke, head injury and other ischemic events.

The following examples are provided for the purpose of illustrating the present invention without, however, limiting the same thereto.

EXAMPLE 1

Cloning of a full length para cDNA

A series of full length para cDNA clones were obtained by PCR amplification of three overlapping regions of the para cDNA followed by assembly of a composite full length clone as outlined in FIG. 1. A detailed description of the scheme used follows. Attempts to amplify the entire 6500 bp para cDNA in a single PCR reaction were unsuccessful; therefore, a number of para cDNAs were generated from a series of three overlapping PCR generated fragments (FIG. 1). Oligonucleotide primers were designed based on the known para cDNA sequence (Loughney et al. 1989, Molecular analysis of the para locus, a sodium channel gene in Drosophila. Cell 58:1143–1154; Thackeray and Ganetzky 1994, Developmentally Regulated alternative splicing generates a complex array of Drosophila para sodium channel isoforms. J. Neuroscience 14:2569–2578) and the primer sequences were primer 1- GACTCTAGACGTTGGCCGCATAGACAATGACAG
[SEQ. ID. NO.: 1], primer 2- AAGAGCTCGACGAAGGGATCG
[SEQ. ID. NO.: 2], primer 3- TCTTCGATCCCTTCGTCGAGCTCT
[SEQ. ID. NO.: 3], primer 4- AAAGGATCCAAATATGATGAA
[SEQ. ID. NO.: 4], primer 5- TTTGGATCCTTTTTCACACTCAATC
[SEQ. ID. NO.: 5], primer 6-
GACTCTAGAGCTAATACTCGCGTGCATCTTGG [SEQ. ID. NO.: 6].

A number of independent PCR generated para cDNA fragments for each segment were isolated and subcloned into the pBluescript SK(+) vector (Stratagene). These para cDNA fragments were assembled into five different full length para cDNA clones with different combinations of alternative exons in the first two fragments, but the 3' fragment of each clone was identical.

Sequence analysis of the PCR generated cDNA clones revealed that they contained a number of PCR induced nucleotide substitutions resulting in alteration and truncation of the encoded para protein; and therefore, these cDNA clones could not be used for functional expression. A cDNA clone suitable for functional expression was constructed by combining existing PCR generated cDNA clones, an existing cDNA clone isolated from a Drosophila head specific cDNA library (Loughney et al. 1989, supra) and new PCR generated cDNA clones as outlined in FIG. 2. The nucleotide sequence of the para cDNA insert in pGH19-13-5 was determined to confirm that it encoded a full length para protein.

A 6513 bp composite para cDNA clone used for functional expression has the following nucleotide sequence:

```
TCTAGACGTTGGCCGCATAGACAATGACAGAAGATTCCGACTCGATATCT
GAGGAAGAACGCAGTTTGTTCCGTCCCTTTACCCGCGAATCATTGGTGCA
AATCGAACAACGCATTGCCGCTGAACATGAAAAGCAGAAGGAGCTGGAAA
GAAAGAGAGCCGAGGGAGAGGTGCCGCGATATGGTCGCAAGAAAAAACAA
AAAGAAATCCGATATGATGACGAGGACGAGGATGAAGGTCCACAACCGGA
TCCTACACTFGAACAGGGTGTGCCAATACCTGTTCGATTGCAGGGCAGCT
TCCCGCCGGAATTGGCCTCCACTCCTCTCGAGGATATCGATCCCTACTAC
AGCAATGTACTGACATTCGTAGTTGTAAGCAAAGGAAAAGATATTTTTCG
CTTTTCTGCATCAAAAGCAATGTGGATGCTCGATCCATTCAATCCGATAC
GTCGTGTGGCCATTTACATTCTAGTGCATCCATTATTTTCCCTATTCATC
ATCACCACAATTCTCGTCAACTGCATCCTGATGATAATGCCGACAACGCC
CACGGTTGAGTCCACTGAGGTGATATTCACCGGAATCTACACATTTGAAT
CAGCTGTTAAAGTGATGGCACGAGGTTTCATTTTATGCCCGTTTACGTAT
CTTAGAGATGCATGGAATTGGCTGGACTTCGTAGTAATAGCTTTAGCTTA
TGTGACCATGGGTATAGATTTAGGTAATCTAGCAGCCCTGCGAACGTTTA
GGGTGCTGCGAGCGCTTAAAACCGTAGCCATTGTGCCAGGCTTGAAGACC
ATCGTCGGCGCCGTCATCGAATCGGTGAAGAATCTGCGCGATGTGATTAT
CCTGACCATGTTCTCCCTGTCGGTGTTCGCGTTGATGGGCCTACAGATCT
ATATGGGCGTGCTCACCGAGAAGTGCATCAAGAAGTTCCCGCTGGACGGT
TCCTGGGGCAATCTGACCGACGAGAACTGGGACTATCACAATCGCAATAG
CTCCAATTGGTATTCCGAGGACGAGGGCATCTCATTTCCGTTATGCGGCA
ATATATCCGGTGCGGGGCAATGCGACGACGATTACGTGTGCCTGCAGGGG
TTTGGTCCGAATCCGAATTATGGCTACACCAGCTTCGATTCGTTCGGATG
GGCTTTCCTGTCCGCCTTCCGGCTGATGACACAGGACTTCTGGGAGGATC
TGTACCAGCTGGTGTTGCGCGCCGCCGGACCATGGCACATGCTGTTCTTT
ATAGTCATCATCTTCCTAGGTTCATTCTATCTTGTGAATTTGATTTTGGC
CATTGTTGCCATGTCGTATGACGAATTGCAAAGGAAGGCCGAAGAAGAAG
AGGCTGCCGAAGAGGAGGCGATACGTGAAGCGGAAGAAGCTGCCGCCGCC
```

```
AAAGCGGCCAAGCTGGAGGAGCGGGCCAATGCGCAGGCTCAGGCAGCAGC
GGATGCGGCTGCCGCCGAAGAGGCTGCACTGCATCCGGAAATGGCCAAGA
GTCCGACGTATTCTTGCATCAGCTATGAGCTATTTGTTGGCGGCGAGAAG
GGCAACGATGACAACAACAAAGAGAAGATGTCCATTCGGAGCGTCGAGGT
GGAGTCGGAGTCGGTGAGCGTTATACAAAGACAACCAGCACCTACCACAG
CACACCAAGCTACCAAAGTTCGTAAAGTGAGCACGACATCCTTATCCTTA
CCTGGTTCACCGTTTAACATACGCAGGGGATCACGTAGTTCTCACAAGTA
CACGATACGGAACGGACGTGGCCGCTTTGGTATACCCGGTAGCGATCGTA
AGCCATTGGTATTGTCAACATATCAGGATGCCCAGCAGCACTTGCCCTAT
GCCGACGACTCGAATGCCGTCACCCCGATGTCCGAAGAGAATGGGGCCAT
CATAGTGCCCGTGTACTATGGCAATCTAGGCTCCCGACACTCATCGTATA
CCTCGCATCAGTCCCGAATATCGTATACCTCACATGGCGATCTACTCGGC
GGCATGGCCGTCATGGGCGTCAGCACAATGACCAAGGAGAGCAAATTGCG
CAACCGCAACACACGCAATCAATCAGTGGGCGCCACCAATGGCGGCACCA
CCTGTCTGGACACCAATCACAAGCTCGATCATCGCGACTACGAAATTGGC
CTGGAGTGCACGGACGAAGCTGGCAAGATTAAACATCATGACAATCCTTT
TATCGAGCCCGTCCAGACACAAACGGTGGTTGATATGAAAGATGTGATGG
TCCTGAATGACATCATCGAACAGGCCGCTGGTCGGCACAGTCGGGCAAGC
GATCGCGGTGTCTCCGTTTACTATTTCCCAACAGAGGACGATGACGAGGA
TGGGCCGACGTTCAAAGACAAGGCACTCGAAGTGATCCTCAAAGGCATCG
ATGTGTTTTGTGTGTGGGACTGTTGCTGGGTTTGGTTGAAATTTCAGGAG
TGGGTATCGCTCATCGTCTTCGATCCCTTCGTCGAGCTCTTCATCACGCT
GTGCATTGTGGTCAACACGATGTTCATGGCAATGGATCACCACGATATGA
ACAAGGAGATGGAACGCGTGCTCAAGAGTGGCAACTATTTCTTCACCGCC
ACCTTTGCCATCGAGGCCACCATGAAGCTAATGGCCATGAGCCCCAAGTA
CTATTTCCAGGAGGGCTGGAACATCTTCGACTTCATTATCGTGGCCCTAT
CGCTATTGGAACTGGGACTCGAGGGTGTCCAGGGTCTGTCCGTATTGCGT
TCCTTTCGATTGCTGCGTGTATTCAAACTGGCCAAGTCTTGGCCCACACT
TAATTTACTCATTTCGATTATGGGACGCACCATGGGCGCTTTGGGTAATC
TGACATTTGTACTTTGCATTATCATCTTCATCTTTGCGGTGATGGGAATG
CAACTGTTCGGAAAGAATTATCATGATCACAAGGACCGCTTTCCGGATGG
CGACCTGCCGCGCTGGAACTTCACCGACTTTATGCACAGCTTCATGATCG
TGTTCCGGGTGCTCTGCGGAGAATGGATCGAGTCCATGTGGGACTGCATG
TACGTGGGCGATGTCTCGTGCATTCCCTTCTTCTTGGCCACCGTTGTCAT
CGGCAATCTTGTGGTACTTAACCTTTTCTTAGCCTTGCTTTTGTCCAATT
TTGGCTCATCTAGCTTATCAGCGCCGACTGCCGATAACGATACGAATAAA
ATAGCCGAGGCCTTCAATCGAATTGGCCGATTTAAAAGTTGGGTTAAGCG
TAATATTGCTGATTGTTTCAAGTTAATACGTAACAAATTGACAAATCAAA
TAAGTGATCAACCATCAGGTGAGAGGACCAACCAGATCAGTTGGATTTGG
AGCGAAGAGCATGGTGACAACGAACTGGAGCTGGGCCACGACGAGATCCT
CGCCGACGGCCTCATCAAGAAGGGGATCAAGGAGCAGACGCAACTGGAGG
TGGCCATCGGGGATCGGATGGAATTCACGATACACGGCGACATGAAGAAC
AACAAGCCGAAGAAATCCAAATATCTAAATAACGCAACGATGATTGGCAA
CTCAATTAACCACCAAGACAATAGACTGGAACACGAGCTAAACCATAGAG
GTTTGTCCTTACAGGACGACGACACTGCCAGCATTAACTCATATGGTAGC
CATAAGAATCGACCATTCAAGGACGAGAGCCACAAGGGCAGCGCCGAGAC
GATGGAGGGCGAGGAGAAGCGCGACGCCAGCAAGGAGGATTTAGGTCTCG
ACGAGGAACTGGACGAGGAGGGCGAATGCGAGGAGGGCCCGCTCGACGGT
GATATCATTATTCATGCACACGACGAGGATATACTCGATGAATATCCAGC
TGATTGCTGCCCCGATTCGTACTATAAGAAATTTCCGATCTTAGCCGGTG
ACGATGACTCGCCGTTCTGGCAAGGATGGGGCAATTTACGACTGAAAACT
TTTCAATTAATTGAAAATAAATATTTTGAAACAGCTGTTATCACTATGAT
TTTAATGAGTAGCTTAGCTTTGGCATTAGAAGATGTACATCTGCCACAAA
GACCCATACTGCAGGATATTTTATACTATATGGACAGAATATTTACGGTT
ATATTCTTCTTGGAAATGTTAATCAAGTGGTTGGCGCTCGGCTTCAAAGT
GTACTTCACCAACGCGTGGTGTTGGCTCGATTTCGTGATTGTCATGGTAT
CGCTTATCAACTTCGTTGCTTCACTTGTTGGAGCTGGTGGTATTCAAGCC
TTCAAGACTATGCGAACGTTAAGAGCACTGAGACCACTACGTGCCATGTC
CCGTATGCAGGGCATGAGGGTCGTCGTTAATGCGCTGGTACAAGCTATAC
CGTCCATCTTCAATGTGCTATTGGTGTGTCTAATATTTTGGCTAATTTTT
GCCATAATGGGTGTACAGCTTTTTGCTGGAAAATATTTTAAGTGCGAGGA
CATGAATGGCACGAAGCTCAGCCACGAGATCATACCAAATCGCAATGCCT
GCGAGAGCGAGAACTACACGTGGGTGAATTCAGCAATGAATTTCGATCAT
GTAGGTAACGCGTATCTGTGCCTTTTCCAAGTGGCCACCTTCAAAGGCTG
GATACAAATCATGAACGATGCTATCGATTCACGAGAGGTGGACAAGCAAC
CAATTCGTGAAACGAACATCTACATGTATTTATATTTCGTATTCTTCATC
ATATTTGGATCCTTTTTCACACTCAATCTGTTCATTGGTGTTATCATTGA
TAATTTTAATGAGCAAAAGAAAAAAGCAGGTGGATCATTAGAAATGTTCA
TGACAGAAGATCAGAAAAAGTACTATAATGCTATGAAAAAGATGGGCTCT
AAAAAACCATTAAAAGCCATTCCAAGACCAAGGTGGCGACCACAAGCAAT
AGTCTTTGAAATAGTAACCGATAAGAAATTCGATATAATCATTATGTTAT
TCATTGGTCTGAACATGTTCACCATGACCCTCGATCGTTACGATGCGTCG
GACACGTATAACGCGGTCCTAGACTATCTCAATGCGATATTCGTAGTTAT
TTTCAGTTCCGAATGTCTATTAAAAATATTCGCTTTACGATATCACTATT
TTATTGAGCCATGGAATTTATTTGATGTAGTAGTTGTCATTTTATCCATC
TTAGGTCTTGTACTTAGCGATATTATCGAGAAGTACTTCGTGTCGCCGAC
CCTGCTCCGAGTGGTGCGTGTGGCGAAAGTGGGCCGTGTCCTTCGACTGG
TGAAGGGAGCCAAGGGCATTCGGACACTGCTCTTCGCGTTGGCCATGTCG
CTGCCGGCCCTGTTCAACATCTGCCTGCTGCTGTTCCTGGTCATGTTCAT
CTTTGCCATTTTCGGCATGTCGTTCTTCATGCACGTGAAGGAGAAGAGCG
```

```
GCATTAACGACGTCTACAACTTCAAGACCTTTGGCCAGAGCATGATCCTG
CTCTTTCAGATGTCGACGTCAGCCGGTTGGGATGGTGTACTGGACGCCAT
TATCAATGAGGAAGCATGCGATCCACCCGACAGCGACAAAGGCTATCCGG
GCAATTGTGGTTCAGCGACCGTTGGAATAACGTTTCTCCTCTCATACCTA
GTTATAAGCTTTTTGATAGTTATTAATATGTACATTGCTGTCATTCTCGA
GAACTATAGTCAGGCCACCGAGGACGTGCAAGAGGGTCTAACCGACGACG
ACTACGACATGTACTATGAGATCTGGCAGCAATTCGATCCGGAGGGCACC
CAGTACATACGCTATGATCAGCTGTCCGAATTCCTGGACGTACTGGAGCC
CCCGCTGCAGATCCACAAACCGAACAAGTACAAGATCATATCGATGGACA
TACCCATCTGTCGCGGTGACCTCATGTACTGCGTGACATCCTCGACGCC
CTTACGAAAGACTTCTTTGCGCGGAAGGGCAATCCGATAGAGGAGACGGG
TGAGATTGGTGAGATAGCGGCCCGCCCGGATACGGAGGGCTACGAGCCCG
TCTCATCAACGCTGTGGCGTCAGCGTGAGGAGTACTGCGCCCGGCTAATC
CAGCACGCCTGGCGAAAGCACAAGGCGCGCGGCGAGGGAGGTGGGTCCTT
TGAGCCGGATACGGATCATGGCGATGGCGGTGATCCGGATGCCGGGGACC
CGGCGCCCGATGAAGCAACGGACGGCGATGCGCCCGCTGGTGGAGATGGT
AGTGTTAACGGTACTGCAGAAGGAGCTGCCGATGCCGATGAGAGTAATGT
AAATAGTCCGGGTGAGGATGCAGCGGCGGCGGCAGCAGCAGCAGCAGCAG
CGGCGGCGGCGGGCACGACGACGGCGGGAAGTCCCGGAGCGGGTAGCGCC
GGGCGACAGACCGCCGTTCTCGTGGAGAGCGACGGGTTCGTGACGAAGAA
CGGCCACAAGGTGGTCATCCACTCGCGATCGCCGAGCATCACGTCGCGCA
CGGCGGATGTCTGAGCCAGGCCTCGCCCCCCCCTCCAAGATGCACGCGAG
TATTAGCTCTAGA[SEQ. ID. NO.: 7].
```

EXAMPLE 2

In Vitro Synthesis of para and tipE Synthetic mRNA for In Vitro or In Vivo Translation The protocol for the production of para and tipE synthetic mRNA is identical. Synthetic mRNA is produced in sufficient quantity in vitro by cloning double stranded DNA encoding para and tipE mRNA into a plasmid vector containing a bacteriophage promoter, linearizing the plasmid vector containing the cloned para-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

It may be advantageous to synthesize mRNA containing a 5' terminal cap structure and a 3' poly A tail to improve mRNA stability. A cap structure, or 7-methylguanosine, may be incorporated at the 5' terminus of the mRNA by simply adding 7-methylguanosine to the reaction mixture with the DNA template. The DNA-dependent RNA polymerase incorporates the cap structure at the 5' terminus as it synthesizes the mRNA. The poly-A tail is found naturally occurring in many cDNAs but can be added to the 3' terminus of the mRNA by simply inserting a poly A tail-encoding DNA sequence at the 3' end of the DNA template.

Figure 2:
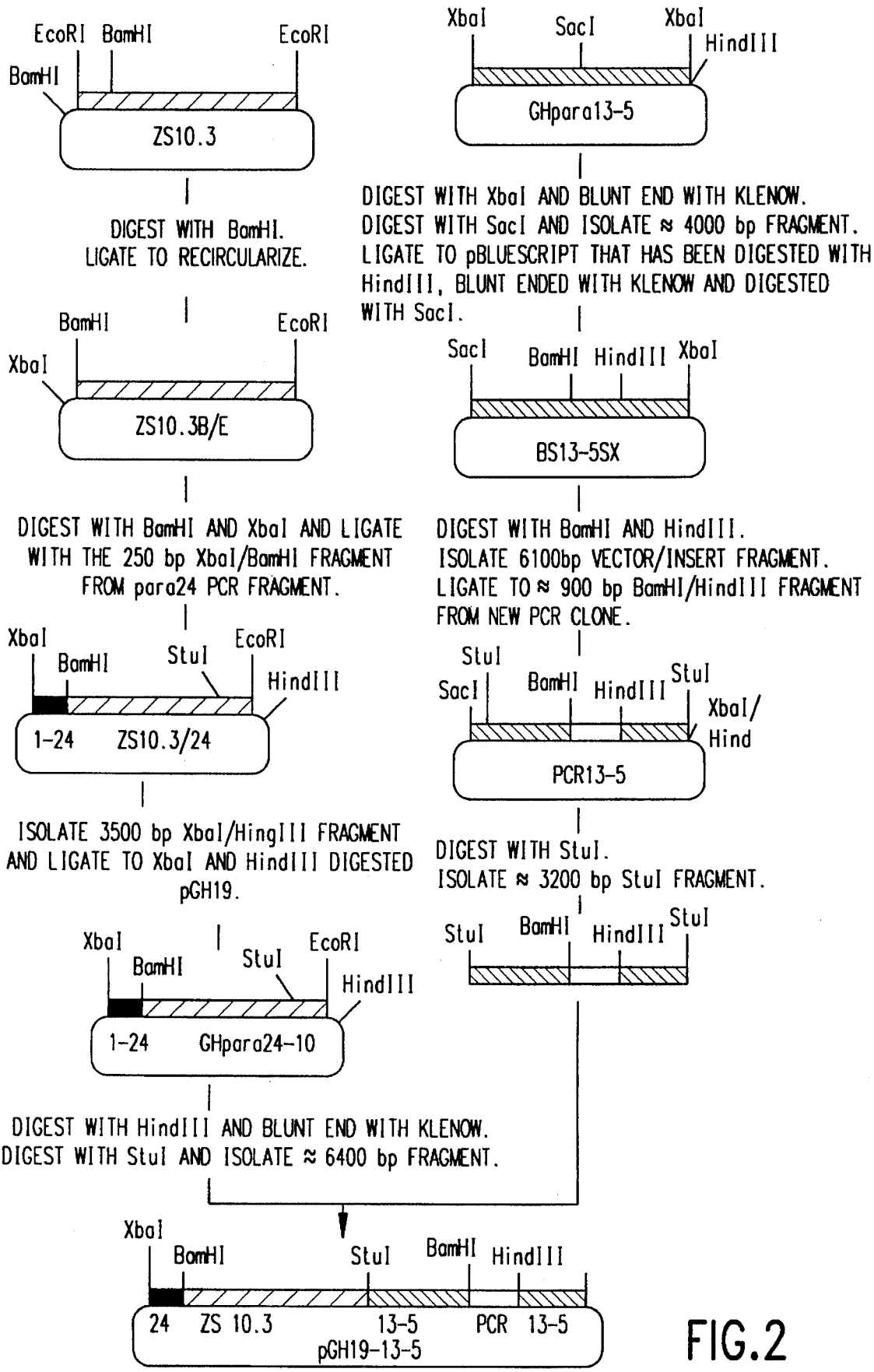
FIG. 2—Construction of a functional full length para cDNA is shown.
Figure 3A:
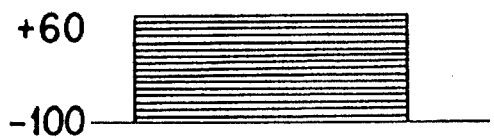
FIG. 3 Panels A, B, C and D—Expression of tetrodotoxin-sensitive sodium currents in Xenopus oocytes injected with para and ripe mRNA produced by in vitro transcription is shown.
Figure 3B:
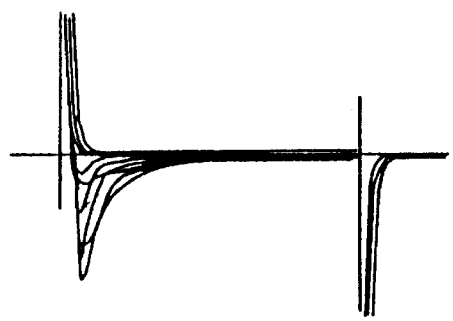
Figure 3C:
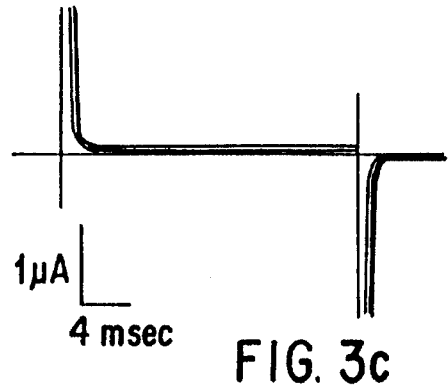
Figure 3D:
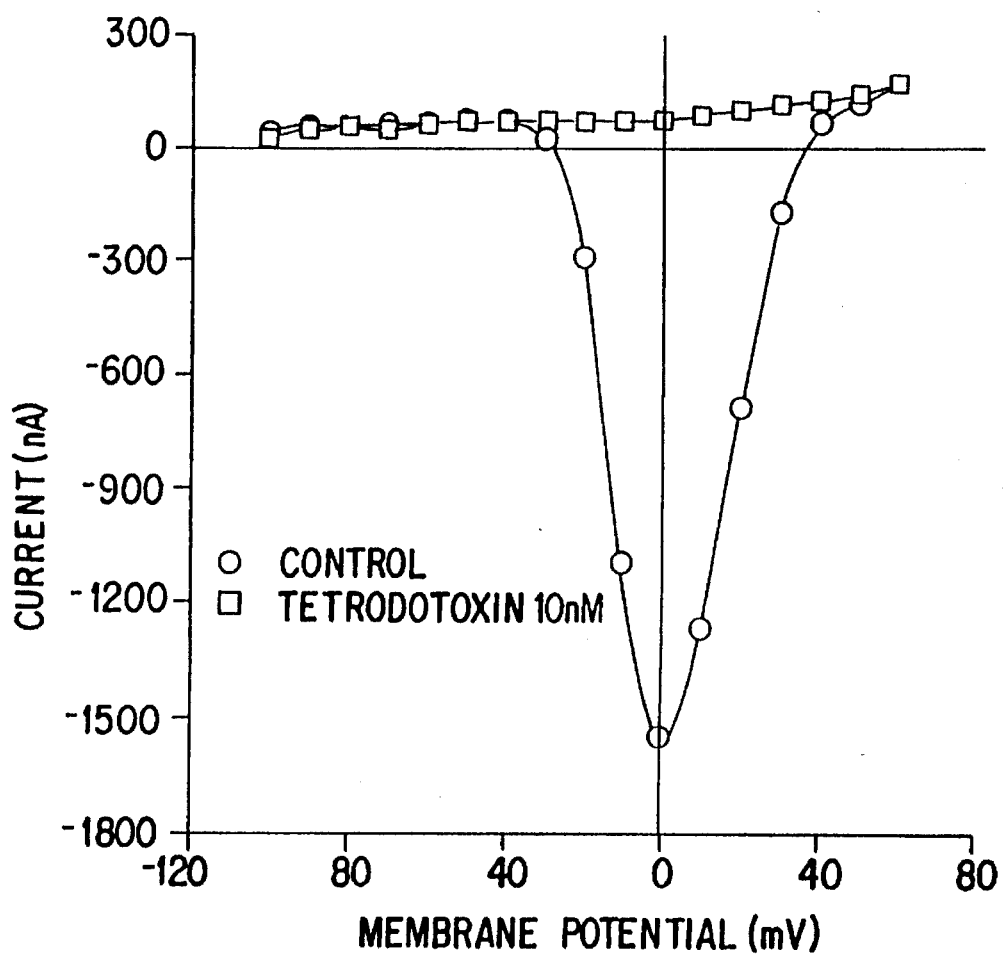

The 6513 bp double stranded para encoding DNA was subcloned into the bacteriophage containing vector pGH19 as described in FIG. 2. The pGH19 vector was derived from of the pGEMHE vector (Liman et al., 1992, Subunit stoichiometry of a mammalian K+ Channel determined by construction of multimeric cDNAs. Neuron 9:861-871) by inserting NotI and XhoI restriction enzyme sites between the unique PstI and NheI sites of pGEMHE (Evan Goulding and Steve Siegelbaum, Columbia University). The plasmid vector containing the cloned para-encoding DNA was linearized with the restriction enzyme NotI and in vitro synthesized para mRNA containing a 5' terminal cap structure was synthesized using either the mMessage mMachine (Ambion) or mCAP (Stratagene) kits per manufacturer's instructions.

The isolated and purified para and tipE mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes were microinjected with a sufficient amount of synthetic para and tipE mRNA to produce para and tipE protein. The synthetic para and tipE mRNAs were injected into Xenopus oocytes by standard procedures and were analyzed for para and tipE expression as described below.

EXAMPLE 3

Characterization Of para voltage-activated sodium channels in *Xenopus oocytes*

*Xenopus laevis* oocytes were prepared and injected using standard methods previously described and known in the an [Arena, J. P., Liu, K. K., Paress, P. S. & Cully, D. F. Mol. Pharmacol. 40, 368-74 (1991); Arena, J. P., Liu, K. K., Paress, P. S., Schaeffer, J. M. & Cully, D. F. Mol. Brain Res. 15; 339-348 (1992)]. Adult female *Xenopus laevis* were anesthetized with 0.17% tricaine methanesulfonate and the ovaries were surgically removed and placed in a dish consisting of (mM): NaCl 82.5, KCl 2, MgCl2 1, CaCl2 1.8, HEPES 5 adjusted to pH 7.5 with NaOH (OR-2). Ovarian lobes were broken open, rinsed several times, and gently shaken in OR-2 containing 0.2% collagenase (Sigma, Type IA) for 2-5 hours. When approximately 50% of the follicular layers were removed, Stage V and VI oocytes were selected and placed in media consisting of (mM): NaCl 86, KCl 2, MgCl2 1, CaCl2 1.8, HEPES 5, Na pyruvate 2.5, theophylline 0.5, gentamicin 0.1 adjusted to pH 7.5 with NaOH (ND-96) for 24-48 hours before injection. Oocytes were injected with 50 nl of para RNA (50-250 ng) and/or tipE RNA (50-250 ng). Control oocytes were injected with 50 nl of water. Oocytes were incubated for 2-10 days in ND-96 before recording. Incubations and collagenase digestion were carried out at 18° C.

Recordings were made at room temperature 2-10 days after injection in standard frog saline consisting of (mM): NaCl 115, KCl 2, MgCl2 1, CaCl2 1.8, HEPES 10 adjusted to pH 7.5 with NaOH. Oocytes were voltage-clamped using a standard two microelectrode amplifier (Dagan 8500 or TEV-200, Minneapolis, Min.). Pipettes were filled with 3M KCl and had resistance's between 0.5–3.0 MΩ. The Plexiglas recording chamber (volume 200 μl) was connected to ground with a Ag/AgCl electrode. Data were acquired and analyzed using the PCLAMP software package with a TL-1 interface (Axon Instruments, Foster City, Calif.). The amplitude of peak voltage-activated sodium currents were determined after subtraction of linear leak currents, or as the tetrodotoxin-sensitive determined after subtraction of the current in the presence of 30 nM tetrodotoxin. Data were filtered at 2–5 kHz and sampled at 10–33 kHz.

Figure 4:
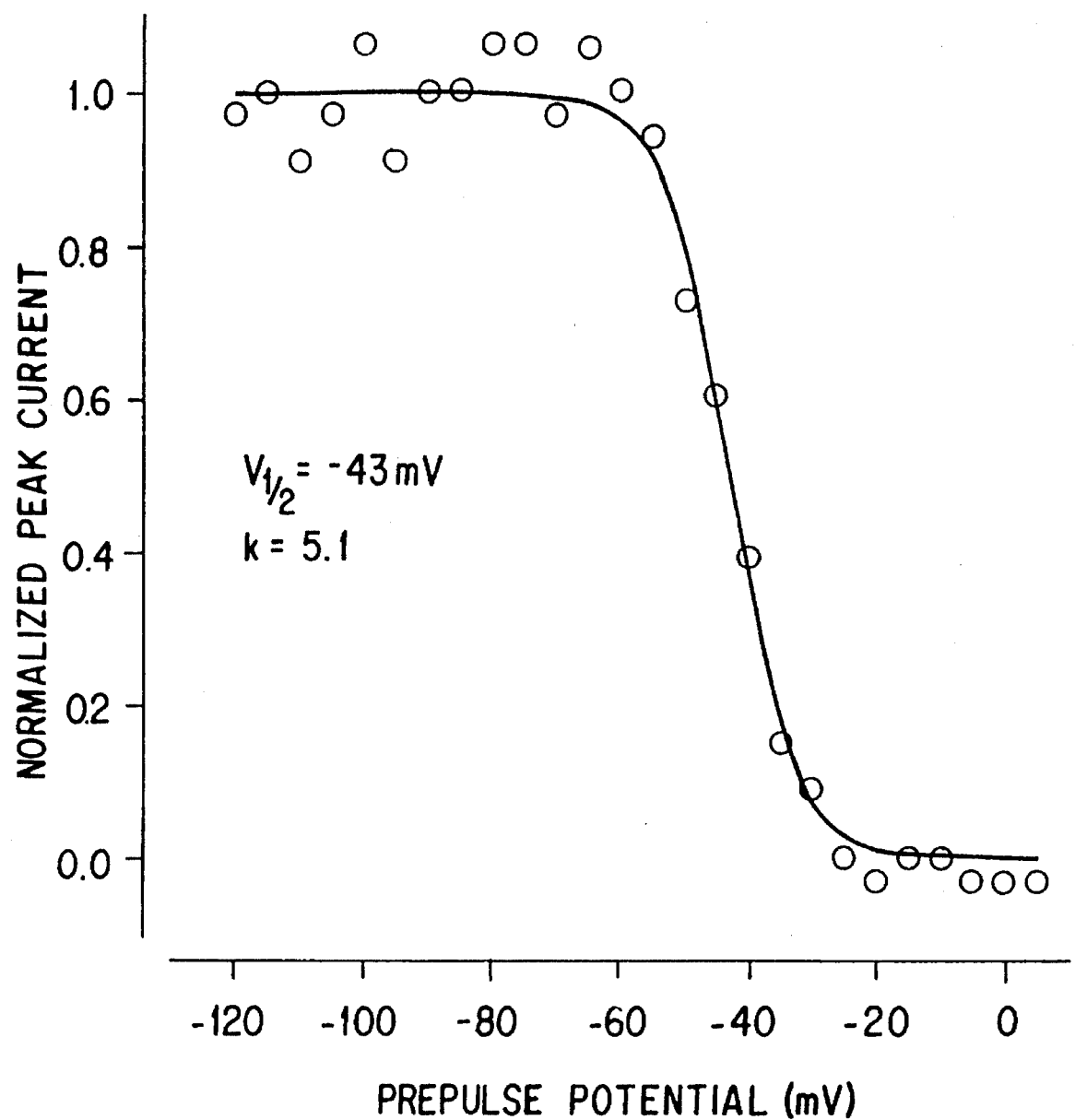
FIG. 4—Steady-state voltage dependence of inactivation for para sodium currents is shown.

Oocytes injected with in vitro RNA for para and tipE expressed voltage-activated sodium currents (FIG. 3). Currents were elicited with 20 sec voltage steps from a holding potential of −100 mV (voltage protocol depicted in FIG. 3a). Oocytes simultaneously expressing para and tipE proteins exhibited the rapidly activating and inactivating inward currents (FIG. 3b). The threshold for current activation was approximately −33±3 mV (n=6), and peak currents were observed at −3±2 mV (n=6). The voltage-activated currents were completely inhibited with 10 nM tetrodotoxin (FIG. 3 Panels B, C, and D n=10). The voltage-dependence of inactivation was also examined (FIG. 4). Test pulses to 0 mV were preceded by 50 msec prepulses to the potentials indicated on the abscissa (FIG. 4). Normalized peak current was plotted as a function of the prepulses potential. The smooth curve is a fit of the data to the function $I=\{1+\exp[(V_m-V_{1/2})/k]\}^{-1}$ where I is the normalized current, $V_m$ is the prepulse potential, $V_{1/2}$ is the point of half-maximal inactivation, and k is the slope factor. $V_{1/2}$ was −42±1 mV with a slope factor of 5.2±0.5 (n=4).

Several lines of evidence demonstrate that the current expressed after coinjection of para and tipE in vitro RNA represents Drosophila voltage-activated sodium currents. First, the current is blocked with tetrodotoxin, a potent selective inhibitor of vertebrate and invertebrate voltage-activated sodium channels [Catterall, W. A. Ann. Rev. Pharmacol. Toxicol. 20:15–43 (1980)]. Similar to the para sodium currents expressed in oocytes, the sodium currents recorded from Drosophila embryonic neurons are completely inhibited with 10 nM tetrodotoxin [O'Dowd, D. K. and Aldrich, R. W. J. Neurosci. 8: 3633–3643 (1988); Saito, M. and Wu, C. F. J Neurosci. 11, 21235–2150 (1991)]. Secondly, very rapid activation and inactivation of the current, the threshold for activation, and the voltage dependence of peak current agree with data previously reported from Drosophila neurons in culture [O'Dowd, D. K. and Aldrich, R. W. J. Neurosci. 8, 3633–3643 (1988); Byerly, L. and Leung, H. T. J. Neurosci. 8: 4379–4393 (1988); Saito, M. and Wu, C. F. J Neurosci. 1 1:2135–2150 (1991)]. Finally, the $V_{1/2}$ and slope of the steady-state inactivation curve was very close to that reported for Drosophila embryonic neurons [O'Dowd, D. K. and Aldrich, R. W. J. Neurosci. 8: 3633–3643 (1988)].

Injection of the individual subunits, para or tipE, failed to express functional homomeric channels. Injection of oocytes with 200–300 ng of an individual subunit RNA resulted in no voltage-activated sodium current for up to 8 days after injection. In contrast, after coinjection of 150 ng of both subunits 50% of the oocytes express voltage-activated sodium currents after 3 days, and 90 % on day 5.

EXAMPLE 4

Cloning of the para and tipE cDNA into E. coli Expression Vectors.

The protocol for the expression of para and tipE in E. coli is identical. Recombinant para is produced in E. coli following the transfer of the para expression cassette into E. coli expression vectors, including but not limited to, the pET series (Novagen). The pET vectors place para expression under control of the tightly regulated bacteriophage T7 promoter. Following transfer of this construct into an E. coli host which contains a chromosomal copy of the T7 RNA polymerase gene driven by the inducible lac promoter, expression of para is induced when an appropriate lac substrate (IPTG) is added to the culture. The levels of expressed para are determined by the assays described above.

The cDNA encoding the entire open reading frame for para or tipE is inserted into the NdeI site of pET [16] 11a. Constructs in the positive orientation are identified by sequence analysis and used to transform the expression host strain BL21. Transformants are then used to inoculate cultures for the production of para and tipE protein. Cultures may be grown in M9 or ZB media, whose formulation is known to those skilled in the art. After growth to an approximate $OD_{600}=1.5$, expression of para or tipE is induced with about 1 mM IPTG for about 3 hours at 37° C.

EXAMPLE 5

Cloning of para and tipE cDNA into Mammalian Expression Vectors

Para and tipE cDNA expression cassettes are ligated at appropriate restriction endonuclease sites to vectors containing strong, universal mammalian promoters, including but not limited to: pcDNA3 (Invitrogen), pBC12BI [Cullen, B. R. Methods in Enzymol. 152:684–704 1988], and pEE12 (CellTech EP 0 338,841), or strong inducible mammalian promoters, including but not limited to, pMAMneo (Clontech).

Cassettes containing the para and tipE cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC#CRL1651), CV-1 [Sackevitz et al., Science 238:1575 (1987)], 293, L cells (ATCC#CRL6362)] by standard methods including but not limited to electroporation, or chemical procedures (cationic liposomes, DEAE dextran, calcium phosphate). Transfected cells and cell culture extracts can be harvested and analyzed for para and tipE expression as described below.

All of the vectors used for mammalian transient expression can be used to establish stable cell lines expressing para and tipE. Unaltered para and tipE cDNA constructs cloned into expression vectors will be expected to program host cells to make intracellular para and tipE protein. The transfection host cells include, but are not limited to, CV-1 [Sackevitz et al., Science 238:1575 (1987)], tk-L [Wigler, et al. Cell 11:223 (1977)], NS/O, and dHFr-CHO [Kaufman and Sharp, J. Mol. Biol. 159: 601, (1982)].

Co-transfection of any vector containing para and tipE cDNA with a drug selection plasmid including, but not limited to G418, aminoglycoside phosphotransferase, pLNCX [Miller, A. D. and Rosman G. J., Biotech News 7:980–990 (1989)]; hygromycin, hygromycin-B phosphotransferase, pLG90 [Gritz. L. and Davies, J., Gene 25:179 (1983)]; APRT, xanthine-guanine phosphoribosyl-transferase, pMAM (Clontech) [Murray, et al., Gene 31:233 (1984)] will allow for the selection of stably transfected clones. Levels of para and tipE are quantitated by the assays described above.

Para and tipE cDNA constructs are ligated into vectors containing amplifiable drug-resistance markers for the production of mammalian cell clones synthesizing the highest possible levels of para and tipE. Following introduction of these constructs into cells, clones containing the plasmid are selected with the appropriate agent, and isolation of an over-expressing clone with a high copy number of the plasmid is accomplished by selection in increasing doses of the agent.

Cells are transfected with para, tipE or both para and tipE. Stable cell clones are selected by growth in the presence of the appropriate selectable marker. Single resistant clones are isolated and shown to contain the intact para or tipE gene or both para and tipE genes. Clones containing the para and tipE cDNAs are analyzed for expression using immunological techniques, such as immunprecipitation, Western blot, and immunofluorescence using antibodies specific to the para and tipE proteins. Antibody is obtained from rabbits inoculated with peptides that are synthesized from the amino acid sequence predicted from the para and tipE sequences. Expression is also analyzed using patch clamp electrophysiological techniques and $^3$H-saxitoxin binding assays.

Cells that are expressing para and tipE, stably or transiently, are used to test for expression of voltage-activated sodium channels and for ligand binding activity. These cells are used to identify and examine other compounds for their ability to modulate, inhibit or activate the para voltage-activated sodium channel as described herein.

Cloning of para and tipE cDNA into Drosophila Expression Vectors

Para and tipE cDNA expression cassettes are ligated at appropriate restriction endonuclease sites to vectors containing constituted or inducible Drosophila promoters, including but not limited to: pRmHa-1 (Bunch et al., 1988, Characterization and use of the Drosophila metallothionein promoter in cultured Drosophila melanogaster cells. Nucleic Acids Research 16:1043–1060) and pCaSpeR-act (Thummel et al., 1988, Vectors for Drosophila P-element -mediated transformation and tissue culture transfection. Gene 74:445–456).

Cassettes containing the para and tipE cDNA in the positive orientation with respect to the promoter are ligated into appropriate restriction sites 3' of the promoter and identified by restriction site mapping and/or sequencing. These cDNA expression vectors are introduced into various host cells including, but not limited to: Schneider-2 and Kc cells by standard methods including but not limited to electroporation, or chemical procedures (cationic liposomes, DEAE dextran, calcium phosphate). Transfected cells and cell culture extracts can be harvested and analyzed for para and tipE expression as described herein.

All of the vectors used for Drosophila transient expression can be used to establish stable cell lines expressing para and tipE. Unaltered para and tipE cDNA constructs cloned into expression vectors will be expected to program host cells to make intracellular para and tipE protein.

Co-transfection of any vector containing para and tipE cDNA with a drag selection plasmid including, but not limited to G418, aminoglycoside phosphotransferase, [Miller, A. D. and Rosman G. J., Biotech News 7:980–990 (1989)];and hygromygin, hygromycin-B phosphotransferase,[Gritz. L. and Davies, J., Gene 25:179 (1983)] will allow for the selection of stably transfected clones. Levels of para and tipE are quantitated by the assays described above.

para and tipE cDNA constructs are ligated into vectors containing amplifiable drag-resistance markers for the production of Drosophila cell clones synthesizing the highest possible levels of para and tipE. Following introduction of these constructs into cells, clones containing the plasmid are selected with the appropriate agent, and isolation of an over-expressing clone with a high copy number of the plasmid is accomplished by selection in increasing doses of the agent.

Cells are transfected with para, tipE or both para and tipE. Stable cell clones are selected by growth in the presence of the appropriate selectable marker. Single resistant clones are isolated and shown to contain the intact para or tipE gene or both para and tipE genes. Clones containing the para and tipE cDNAs are analyzed for expression using immunological techniques, such as immunprecipitation, Western blot, and immunofluorescence using antibodies specific to the para and tipE proteins. Antibody is obtained from rabbits inoculated with peptides that are synthesized from the amino acid sequence predicted from the para and tipE sequences. Expression is also analyzed using patch clamp electrophysiological techniques and 3H-saxitoxin binding assays.

Cells that are expressing para and tipE, stably or transiently, are used to test for expression of voltage-activated sodium channels and for ligand binding activity. These cells are used to identify and examine other compounds for their ability to modulate, inhibit or activate the para voltage-activated sodium channel as described herein.

EXAMPLE 6

Cloning of para and tipE cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL#1711 ). Recombinant baculoviruses expressing para and/or tipE cDNA are produced by the following standard methods (In Vitrogen Maxbac Manual): the para and tipE cDNA constructs are ligated downstream of the polyhedrin promoter in a variety of baculovirus transfer vectors, including the pAC360 and the pBlueBac vector (InVitrogen). Recombinant baculoviruses are generated by homologous recombination following co-transfection of the baculovirus transfer vector and linearized AcNPV genomic DNA [Kitts, P. A., Nuc. Acid. Res.18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of 13-galactosidase expression (Vialard, et al. 1990, J. Virol., 64: 37–50). Following plaque purification and infection of sf9 cells with para and/or tipE recombinant baculovirus, para and tipE expression is measured by the assays described herein.

The cDNA encoding the entire open reading frame for para or tipE is inserted into the BamHI site of pBlueBacII. Constructs in the positive orientation with respect to the polyhedrin promoter are identified by sequence analysis and used to transfect Sf9 cells in the presence of linear AcNPV mild type DNA.

Authentic, active para and tipE is found associated with the membranes of infected cells. Membrane preparations are prepared from infected cells by standard procedures.

EXAMPLE 7

Cloning of para and tipE cDNA into a yeast expression vector

Recombinant para and tipE is produced in the yeast *S. cerevisiae* following the insertion of the optimal para and tipE cDNA construct into expression vectors designed to direct the intracellular expression of heterologous proteins. For intracellular expression, vectors such as EmBLyex4 or the like are ligated to the para or tipE cistron [Rinas, U. et al., Biotechnology 8: 543–545 (1990); Horowitz B. et al., J. Biol. Chem. 265:4189–4192 (1989)]. The levels of expressed para and tipE are determined by the assays described herein.,

EXAMPLE 8

Purification of Recombinant para and tipE

Recombinantly produced para and tipE may be purified by antibody affinity chromatography. para or tipE antibody affinity columns are made by adding the anti-para or anti-tipE antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized para or tipE are slowly passed through the column. The column is then washed with phosphate- buffered saline together with detergents until the optical density (A280) falls to background, then the protein is eluted with 0.23M glycine-HCl (pH 2.6) together with detergents. The purified para or tipE protein is then dialyzed against phosphate buffered saline together with detergents.

EXAMPLE 9

Assay for the identification of para voltage-activated sodium channel modulators.

Modulators of insect sodium channels can be identified by screening for modulators of the para voltage-activated sodium channel. Modulators of insect sodium channel activity can be identified by a variety of approaches, including but not limited to, radioisotopic flux assays, ligand binding assays, and cell viability assays.

Measuring Na channel activity in cell populations by monitoring radioisotopic flux is a well established technique (Catterall, W. A. *Journal of Biological Chemistry* 252, 8669–8676 (1977); Tamkun, M. M. & Caterall, W. A. *Molecular Pharmacology* 19; 78–86 (1981 )). Using transfected cell lines (see above) expressing the para voltage-activated sodium channel, modulators of the Drosophila voltage-activated sodium channel are isolated in a [22Na] flux assay in a 96-well format. To identify sodium channel agonists, para transfected cells are aliquoted into each well of a 96-well microtiter dish and [22Na] is added to the culture media, test compounds are added to each well and agonists are identified by an increase in [22Na] uptake as compared to untreated cells. Specificity is determined by blocking [22Na] uptake with tetrodotoxin. Likewise, sodium channel antagonist can be identified by screening for compounds that block [22Na] uptake following activation of the para voltage-activated sodium channel.

Sodium channel modulators can also be identified by measuring the toxicity of Na channel activators on para expressing cells. Sodium channel activators are toxic because prolonged activation of sodium channels causes osmotic lysis of the cells. Sodium channel blockers are detected by their ability to protect from the toxicity of Na channel activators (Manger, R. L., Leja, L. S., Lee, S. Y., Hungerford, J. M. & Wekell, M. M. *Analytical Biochemistry* 214, 190–194 (1993)). The assay is performed in 96 well plates and toxicity is measured by employing a plate reader with a membrane-impermeant reporter, such as ethidium bromide homodimer (the methodology is described in a product application note from Molecular Probes for the Live/Dead Eukolight Cytotoxicity kit). The specificity of sodium channel activators is determined by blocking toxicity with tetrodotoxin, a highly potent and selective sodium channel blocker.

---

What is claimed is:

1. A DNA molecule characterized by the nucleotide sequence as set forth in SEQ ID NO:7.

2. An expression vector containing the DNA molecule of claim 1.

3. A recombinant host cell containing the expression vector of claim 2.

* * * * *